United States Patent [19]

Kurtz et al.

[11] 4,258,824
[45] Mar. 31, 1981

[54] SOUND MUFFLING BAFFLE FOR DRAINAGE DEVICE

[75] Inventors: Leonard D. Kurtz, Woodmere; Robert E. Bidwell, Melville, both of N.Y.

[73] Assignee: BioResearch Inc., Farmingdale, N.Y.

[21] Appl. No.: 5,512

[22] Filed: Jan. 22, 1979

[51] Int. Cl.³ .................. A61M 1/00; G10K 11/00
[52] U.S. Cl. ............................ 181/233; 128/276
[58] Field of Search .............. 181/233, 235; 128/276

[56] References Cited

U.S. PATENT DOCUMENTS

| | | | |
|---|---|---|---|
| 2,169,359 | 8/1939 | Jones et al. | 181/233 |
| 2,485,908 | 10/1949 | Morrow | 181/235 |
| 3,363,626 | 1/1968 | Bidwell et al. | 128/276 |
| 3,474,782 | 10/1969 | Cupp | 181/235 |
| 3,559,647 | 2/1971 | Bidwell et al. | 128/276 |
| 3,568,672 | 3/1971 | Cupp | 181/235 |
| 3,683,913 | 8/1972 | Kurtz et al. | 128/276 |
| 3,782,497 | 1/1974 | Bidwell et al. | 181/233 |
| 3,783,870 | 1/1974 | Schachet | 128/276 |

*Primary Examiner*—George H. Miller, Jr.
*Assistant Examiner*—Benjamin R. Fuller
*Attorney, Agent, or Firm*—Larson, Taylor and Hinds

[57] ABSTRACT

A drainage device is provided for draining fluid from a body cavity and for use with a vacuum. The drainage device has three chambers, a collection chamber, a water seal chamber and a pressure regulating manometer chamber. In operation, air bubbles passing through a body of liquid in the manometer chamber produces a disturbing sound. The present invention provides a sound muffling baffle plate including a plurality of fine apertures which is disposed in the lower end portion of the large arm of the manometer chamber, which prevents the formation of large air bubbles and effectively muffles the sounds emanating from the device during use.

1 Claim, 2 Drawing Figures

SOUND MUFFLING BAFFLE FOR DRAINAGE DEVICE

BACKGROUND OF THE INVENTION

This invention relates to drainage devices and more particularly to underwater drainage devices of the type disclosed in U.S. Pat. Nos. 3,363,626 and 3,363,627. More specifically, the invention relates to the prevention of noise in such underwater drainage devices as disclosed in the aforementioned patents when used with suction wherein prior art devices substantial noise is produced by the device during operation by reason of air bubbling through the water in the manometer chamber. The present invention provides muffling means for reducing the noise produced by such bubbling to an acceptable level.

In our prior U.S. Pat. No. 3,782,497, there is disclosed a sound muffling device including a member which is inserted in the opening to atmosphere from the manometer chamber. This member is provided with a tortuous passageway extending therethrough and such device to a certain extent muffles the sound emanating from the device by reason of the bubbling of gas through the water in the manometer chamber. However, the sound muffling device disclosed in U.S. Pat. No. 3,782,497 is not entirely satisfactory in reducing the sound from underwater drainage devices to a level which is acceptable to patients. Accordingly, it became necessary to improve upon such device.

SUMMARY OF THE INVENTION

The present invention provides an apertured baffle plate in the large arm of the manometer chamber. This baffle plate extends across the entire cross section of the large arm of the water seal chamber adjacent the lower end thereof and is provided with a plurality of fine holes therein. This apertured baffle plate serves to break up the air which is passing into the large arm of the manometer chamber from the opening to atmosphere in the small arm of the manometer into a large number of small bubble streams so that there are no large air bubbles formed in the water in the large arm of the manometer chamber.

It has been found that the high noise level which has been produced in underwater drainage devices of the type shown in the aforementioned patents is caused by the formation of large air bubbles in the water in the large arm of the manometer chamber and in the breaking up of these large bubbles at the surface of the water in the large arm of the manometer chamber. Thus, by providing a means which prevents the formation of the large air bubbles, this noise problem has been obviated.

Prior U.S. Pat. Nos. 3,559,647; 3,683,913 and 3,782,497 all disclose underwater drainage devices with air flow meters disposed therein. Such air flow meters comprise a number of holes formed in a plate in the large arm of the manometer chamber and in the large arm of the water seal chamber. Such a series of apertures provide a means for determining the quantity of air passing through the manometer chamber and through the water seal chamber. However, these devices do not perform the same function as the presently disclosed sound muffling baffle plate inasmuch as the apertures in these prior art devices are not sufficiently small to prevent the formation of large air bubbles.

An object of the present invention is to provide a sound muffling system for an underwater drainage device which reduces the noise caused by air bubbling through the water in the manometer chamber to an acceptable level.

Another object of the present invention is to provide in an underwater drainage device a plate having a plurality of fine holes therein in the lower end of the large arm of the manometer chamber which performs the function of breaking up the large air bubbles normally formed in the water in the manometer chamber into streams of small bubbles so as to reduce the noise produced by the drainage device during operation.

Other objects and many of the attendant advantages of the present invention will become more readily apparent upon consideration of the following detailed specification.

DETAILED DESCRIPTION OF THE INVENTION

There follows a detailed description of a preferred embodiment of the invention, together with accompanying drawings. However, it is to be understood that the detailed description and accompanying drawings are provided solely for the purpose of illustrating a preferred embodiment and that the invention is capable of numerous modifications and variations apparent to those skilled in the art without departing from the spirit and scope of the invention.

Figure 1:
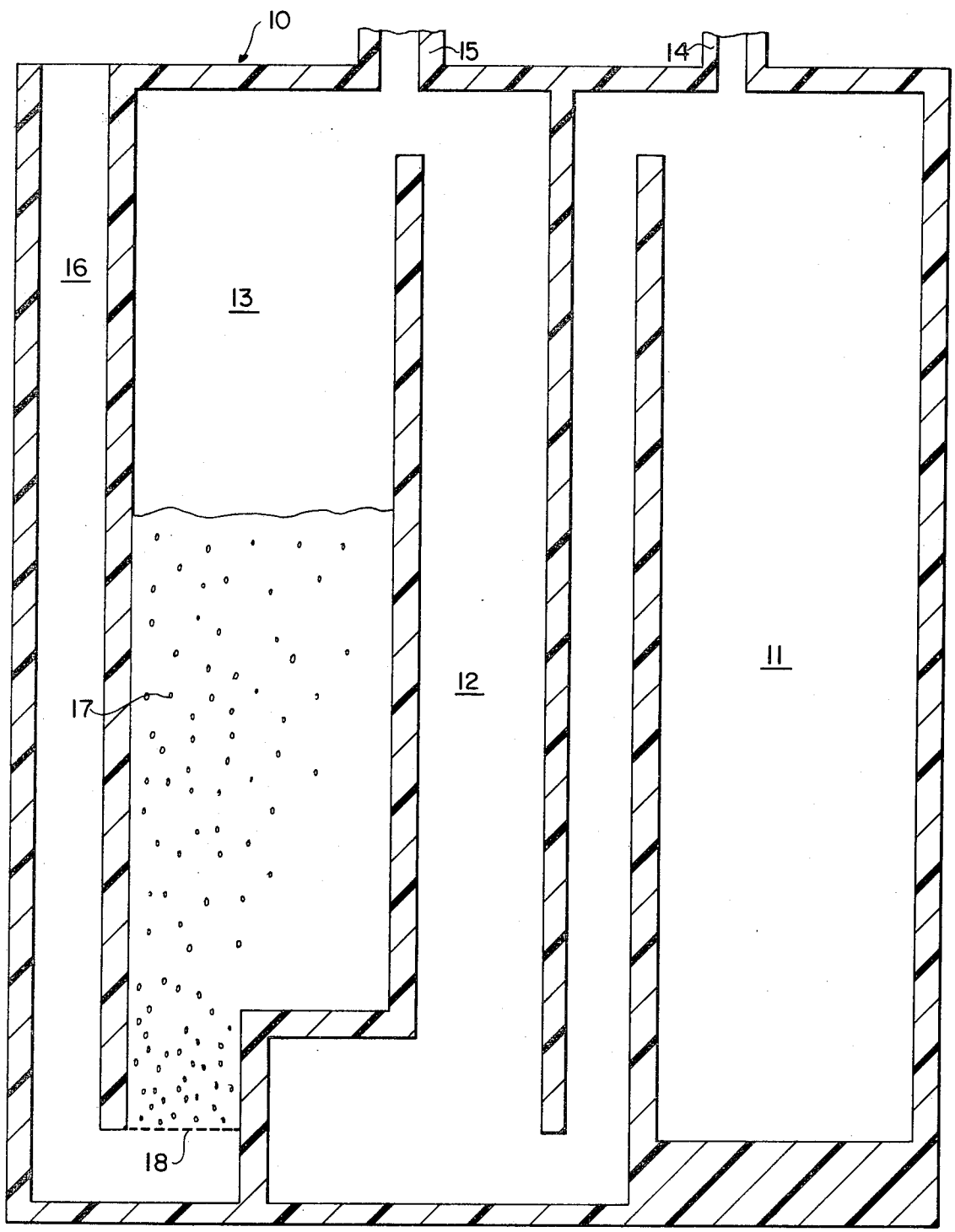
Figure 2:
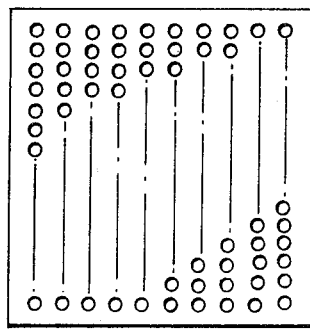

FIG. 1 is a sectional view through the center plane of an underwater drainage apparatus according to the present invention; and FIG. 2 is a plan view of the sound muffling device according to the present invention.

Referring now more specifically to the drawings, there is shown at 10 an underwater drainage device of the general type disclosed in prior U.S. Pat. Nos. 3,363,626 and 3,363,627. Such an underwater drainage device includes three chambers, a collection chamber 11, generally U-shaped underwater seal chamber 12 and a generally U-shaped pressure manometer chamber 13. The collection chamber 11 is provided with an opening 14 which is adapted to be connected to a thoracotomy tube connected to the patient. Liquid from the patient's pleural cavity flows through the thoracotomy tube and is collected in the collection chamber 11 which gases are drawn through the underwater seal chamber 12 and pass out through a connection 15 to a vacuum source.

The manometer chamber 13 comprises a small arm 16 which has the upper end thereof connected to atmosphere and a large arm 17 which has the upper end thereof in communication through connection 15 with the vacuum source and the large arm of the underwater seal chamber 12. The manometer chamber serves to regulate the degree of vacuum maintained within the device by the amount of water in the large arm 17 of the manometer chamber. During operation of the device air passes downwardly through the small arm 16 of the manometer chamber and bubbles through the water in the large arm 17 of the manometer chamber and out through the connection with vacuum source.

The production of large air bubbles passing through the water in the large arm of the manometer chamber and the breaking up of these bubbles as they reach the surface of the water in the chamber causes considerable noise and this has been a source of annoyance to patients. According to the present invention there is provided a perforated plate 18 which extends across the lower end of the large arm of the manometer chamber.

As can be seen in the drawing this plate 18 serves to break up the air passing downwardly through the small arm of the manometer chamber into a series of streams of fine bubbles and the breaking of these fine bubbles on the surface of the water in the large arm of the manometer chamber do not create nearly so great a noise level and thus, disturbance of the patients by the noise of operation of the underwater drainage device is considerably reduced.

The perforated plate 18 is shown in greater detail in FIG. 2 and it can be seen that in the particular embodiment shown the plate is provided with approximately 150 holes of a diameter of 1 millimeter with the plate being essentially square and 26 millimeters in length.

It can be seen that during operation an air plenum 16A is formed beneath the plate 18 and a combination of the air plenum beneath the perforated plate with the fine small holes in the plate prevent the formation of the large air bubbles which have been responsible for the production of objectionable noise levels in prior art devices. The perforated plate extends across the entire cross section of the large arm of the manometer chamber and performs the function of muffling the sounds emanating from the underwater drainage device to such an extent that the rest of patients using the device is not disturbed.

What is claimed is:

1. In a drainage device for draining fluids through a thoracotomy tube from a pleural cavity, said drainage device having a collection chamber having an inlet opening to be placed in fluid communication with a cavity to be drained, a seal chamber having first and second columns in communication with each other at the lower ends thereof and adapted to receive a body of liquid in the lower portion of said first and second seal chamber columns, the upper end of the first seal chamber column being in fluid communication with said collection chamber, the upper end of said second seal chamber column being in fluid communication with a vacuum source, and a manometer chamber comprising first and second columns in fluid communication with each other at the lower ends thereof and adapted to receive a body of liquid in the lower portion of said first and second manometer chamber columns, the upper portion of said first manometer chamber column being in fluid communication with said vacuum source and the upper portion of said second manometer chamber being open to atmosphere, the improvement including means comprising a thin baffle plate extending horizontally across the lower end portion of the first manometer chamber column, said baffle plate having approximately 150 apertures therein of approximately one millimeter in diameter, during operation of the drainage device said baffle plate forming an air plenum beneath the plate and preventing the formation of large noise producing bubbles in the water above the plate.

* * * * *